(12) United States Patent
Mroz (10) Patent No.: US 10,672,148 B2
(45) Date of Patent: Jun. 2, 2020

(54) COMPRESSING AND UNCOMPRESSING METHOD FOR HIGH BIT-DEPTH MEDICAL GRAY SCALE IMAGES

(71) Applicant: AGFA HEALTHCARE, Mortsel (BE)

(72) Inventor: Lukas Mroz, Mortsel (BE)

(73) Assignee: AGFA HEALTHCARE, Mortsel (BE)

( * ) Notice: Subject to any disclaimer, the term of this patent is extended or adjusted under 35 U.S.C. 154(b) by 84 days.

(21) Appl. No.: 15/771,414

(22) PCT Filed: Oct. 27, 2016

(86) PCT No.: PCT/EP2016/075903
§ 371 (c)(1),
(2) Date: Apr. 27, 2018

(87) PCT Pub. No.: WO2017/072218
PCT Pub. Date: May 4, 2017

(65) Prior Publication Data
US 2018/0315215 A1 Nov. 1, 2018

(30) Foreign Application Priority Data
Oct. 30, 2015 (EP) ..................... 15192241

(51) Int. Cl.
*H04N 9/80* (2006.01)
*G06T 9/00* (2006.01)
(Continued)

(52) U.S. Cl.
CPC .............. *G06T 9/00* (2013.01); *G06T 11/001* (2013.01); *H04N 1/41* (2013.01); *H04N 1/465* (2013.01); *H04N 19/117* (2014.11); *H04N 19/186* (2014.11); *H04N 19/196* (2014.11); *G06T 2210/41* (2013.01); *G16H 30/20* (2018.01)

(58) Field of Classification Search
CPC ...... G06T 9/00; G06T 11/001; G06T 2210/41
See application file for complete search history.

(56) References Cited

U.S. PATENT DOCUMENTS 5,148,272 A * 9/1992 Acampora ........... H04N 5/4401
375/240.1
5,381,145 A * 1/1995 Allen .................. H03M 7/4006
341/107

(Continued)

FOREIGN PATENT DOCUMENTS

EP 1 465 418 A1 10/2004
WO 2013/072889 A1 5/2013

OTHER PUBLICATIONS

Official Communication issued in International Patent Application No. PCT/EP2016/075903, dated Jan. 24, 2017.
(Continued)

*Primary Examiner* — Gregory M Desire
(74) *Attorney, Agent, or Firm* — Keating and Bennett, LLP (57) ABSTRACT

A digital encoding and decoding method of high bit-depth gray scale medical images allows standard 3-channel color image compression algorithms to be used to compress and de-compress such encoded high bit-depth gray scale images without significant image quality loss. The digital encoding and decoding method may be used to improve the network transmission, storage and rendering of such gray scale images in a standard web browser.

6 Claims, 7 Drawing Sheets

(51) Int. Cl.
*H04N 19/117* (2014.01)
*H04N 19/196* (2014.01)
*H04N 1/41* (2006.01)
*H04N 19/186* (2014.01)
*H04N 1/46* (2006.01)
*G06T 11/00* (2006.01)
*G16H 30/20* (2018.01)

(56) References Cited

U.S. PATENT DOCUMENTS

| | | | | |
|---|---|---|---|---|
| 6,237,079 B1 * | 5/2001 | Stoney | | G06F 9/3885 |
| | | | | 712/34 |
| 6,721,952 B1 * | 4/2004 | Guedalia | | H04N 21/234318 |
| | | | | 348/588 |
| 6,804,403 B1 * | 10/2004 | Wang | | H04N 19/63 |
| | | | | 375/E7.04 |
| 7,010,044 B2 * | 3/2006 | Dattani | | H04N 19/105 |
| | | | | 375/240.24 |
| 7,233,619 B1 * | 6/2007 | Roman | | H04N 19/93 |
| | | | | 375/240 |
| 8,432,413 B2 * | 4/2013 | Zaharia | | G06F 3/14 |
| | | | | 345/547 |
| 8,442,358 B2 * | 5/2013 | Rankin | | G06T 9/00 |
| | | | | 382/298 |
| 9,516,197 B2 * | 12/2016 | Hogan | | H04N 9/04 |
| 2005/0213751 A1 * | 9/2005 | Apostolopoulos | | H04L 9/065 |
| | | | | 380/28 |
| 2009/0136147 A1 * | 5/2009 | Liau | | H04N 19/60 |
| | | | | 382/246 |
| 2010/0123733 A1 | 5/2010 | Zaharia et al. | | |
| 2012/0179742 A1 * | 7/2012 | Acharya | | H04N 7/18 |
| | | | | 709/202 |
| 2014/0341450 A1 | 11/2014 | Sedan | | |
| 2018/0315215 A1 * | 11/2018 | Mroz | | H04N 19/196 |

OTHER PUBLICATIONS

Shijian Guo et al., "A New Pseudo-coloring Coding Method for DPX Image", 2013 Fourth International Conference on Digital Manufacturing & Automation, DOI: 10.1109/ICDMA.2013.14, Jun. 29, 2013, pp. 54-57.

* cited by examiner

COMPRESSING AND UNCOMPRESSING METHOD FOR HIGH BIT-DEPTH MEDICAL GRAY SCALE IMAGES

CROSS REFERENCE TO RELATED APPLICATIONS

This application is a 371 National Stage Application of PCT/EP2016/075903, filed Oct. 27, 2016. This application claims the benefit of European Application No. 15192241.6, filed Oct. 30, 2015, which is incorporated by reference herein in its entirety.

BACKGROUND OF THE INVENTION

1. Field of the Invention

The present invention relates generally to the compression and decompression of high quality digital gray scale images. The invention presents a method to encode a high quality (high bit-depth) gray scale image in such a way, that the encoded image data can be processed by industry standard image compression algorithms which are being widely used in standard software such as web browsers. As such, the invention presents a method to encode and decode a high quality gray scale image temporarily into a standard 8-bit 3-channel RGB color formatted image file as an intermediary format to store and/or transfer the original gray scale image data in digital computer systems. The use of this intermediary format has the advantage that standard image compression techniques (such as jpeg compression) can be applied to this intermediary format without deteriorating or compromising the image quality of the encapsulated original (typically 10-14-bit) gray scale image.

2. Description of the Related Art

Image data has multiple sampling resolutions. There is a temporal sampling rate, commonly called the frame rate, of motion picture data. Each image also has a vertical and horizontal sampling resolution indicating the number of individual elements, commonly called pixels, in the horizontal and vertical dimensions of the image. This sampling resolution is called the spatial resolution. Each pixel typically is represented by a number of components to define a color. The components may represent luminance and chrominance (YCrCb, for example), or may represent color channels (red, green and blue, or RGB, for example). A value for each component generally is represented using a number of bits called the bit depth. Typical bit depths used for color images are eight bits, and exceptionally ten bits or even sixteen bits.

Diagnostic imaging modalities used in medicine often produce gray scale images using only one single color channel representing the gray scale luminance, and a bit depth of typically ten, twelve or sixteen bits. These bit depths ensure sufficient image quality (i.e. luminance accuracy) to ensure the necessary image processing headroom to perform different contrast enhancement operations on them. However, because of the greater bit depth required per pixel a larger amount of storage or bandwidth is to respectively store or transfer this kind of diagnostic images. Therefore, an unresolved aspect of digital medical imaging is a convenient reduction of this bandwidth required to transfer diagnostic images, while maintaining the required image quality to perform diagnostic work.

The reason why contrast enhancement operations (such as window/level operations) are performed on image data is that the relevant clinical information contained in a diagnostic image may be stored in certain ranges of gray values in the image. The histogram of the image data typically gives an important guidance about where the relevant information is stored in an image for a certain clinical application. A histogram is therefore often used as a basis for automatic contrast enhancement algorithms. The contrast enhancement algorithms are typically interactively applied by a user on the original image data, requiring the original dataset to be available during the contrast enhancement process. This means that the original n-bit image data set has to be available to the viewing software to be able to perform said operations interactively and on-the-fly. This implies that the original n-bit image data have to be transferred somehow to the radiologists' workstation where the diagnostic work is performed.

In order to be able to achieve this, a number of technical constraints have to be taken into consideration. The standard word length of any computer system is 8-bit; this means that the smallest memory storage unit by default is 8 bits long (8 bits=1 byte). On a general-purpose computer, bit paths have a bit depth based on a power of two and are multiples of eight (e.g., eight, sixteen, thirty-two or sixty-four bits). Therefore, 10-bit data generally is converted to 16-bit data before it is processed by the computer. As such, diagnostic images or medical images with bit-depths of 10-, 12- or 16-bits are stored in general in a file format which uses 16-bits per pixel, or 2 bytes per pixel.

Because of this 16-bit per pixel color depth and the usually very high spatial resolutions of diagnostic images, the storage space for archiving, and the bandwidth for transferring these images over a computer network tend to be very high. The high bandwidth requirement has a high impact on the network transfer rates of medical imaging data. A typical consumer of medical imaging data cannot afford to have to wait more than a few seconds to obtain a requested image from a digital archive system. This user requirement forces the developers of medical viewing and archiving systems to look for a balance between image quality and processing performance.

In the art, different solutions have been proposed to balance the image quality against the transferred file size. The chosen strategies typically depend on the intended use of the image in the medical application. For certain applications, it is unacceptable that the spatial resolution is compromised, or that the color space would be unarbitrarily reduced to 8-bit.

Typical solutions to reduce the file size are:
reduction of the spatial resolution of an image file (cropping, scaling down) which reduces the spatial resolution, and thus the quality of the original image
image compression, such as jpeg-compression, which operate on the contents of the image data and which could have a visible impact on the image data
discarding of the least significant bits in an image data set; and thus compressing the image data into an 8-bit format.

After this contrast enhancement process, the resulting data set which is used for display is converted into an 8-bit format anyhow. The reason for this is related to the limitations of the human eye, but also to the technical limitations of standard computer architecture.

It happens that under optimal viewing conditions (very high contrast ratio between black and white) the human eye is only capable of discriminating between at most $2^9$ different shades of gray simultaneously, which is why even diagnostic display systems display medical diagnostic images in 8-bit.

8-bit fits the standard computer architecture limits, which is also applied in the architecture of any display system. (The display system in this context comprises the application software, the operating system, the display driver software, the frame buffer (or video memory) and the actual display or monitor).

Any output system (any display system) is limited to be able to display only 256 shades of gray (or the equivalence of 8 bits of data) at the same time. So, in order to optimally use the data stored in a medical image which was acquired with a higher bit depth then 8, the most relevant information has the be filtered out or selected before it is presented as an 8-bit deep image to the display system.

Another consideration has to be taken into account in the case that viewer software is based on standard web technology, i.e. when web servers and browser are involved in the application delivery to the user. There is a clear advantage in the use of web technology in clinical (or any other) environments. The deployment of the software application happens in a very convenient way from a service and maintenance perspective: web browsers are nowadays highly standardised applications which are deployed on virtually any platform. Software applications running inside a browser are deployed centrally from the web server each time the user wants to access the application. The drawback of web technology is however that the current browser implementations are not designed to support diagnostic imagery, neither to optimize the transfer of high quality diagnostic images to a browser. Medical application developers have to work their way around these existing limitations.

Since standard browsers do not support the special file formats mentioned above natively, a traditional approach to transfer gray scale image data with more than 8 bit precision to viewing software running in a browser is to split the data values from such an image into a low and high byte value which can be stored in two or three 8-bit channels of an RGB image and using lossless compression for transfer [ref to US2010/0123733 A1]. This method is however unable to improve (decrease) the net data size of a high bit depth image as it still transmits or stores the full sixteen bits, as only 10-bits would contain significant image information. Neither can these large files be processed (compressed) natively by the standard image compression algorithms of the browser. This and other methods described in the art thus solve the problem of transferring extended bit depth gray scale images, but are not able to make this transfer more efficient since the data is transferred uncompressed.

Other methods are describing methods for "packing" series of pixel data in different formats. As such, U.S. Pat. No. 6,239,815 describes a method where 10-bit YCrCb data for two pixels is packed into five bytes.

EP 0405885 discloses a recording device which, in one example, divides a 10-bit sample of a digital signal into a word A of the most significant 8 bits and a word B of the least significant 2 bits. Words B of respective samples are combined into a word C of 8 bits, and the words A and C are recorded.

Some of these methods may already improve the total byte consumption for an image, but none of these methods are however using the more efficient compression techniques such as used for color images. Standard browsers are highly efficient and well equipped to perform image compression on regular color images. Unfortunately, these compression algorithms do not work on the altered file formats as described above. Applying the standard image compression algorithms on these gray scale images has a detrimental effect on their clinical quality.

The reason for this loss in quality is that the most popular compression algorithm (lossy JPEG) [JPEG=Joint Photographic Experts Group] makes assumptions on the contents in the image file. The image data of a gray scale image distributed over the different color channels would thus be incorrectly interpreted by the jpeg compression algorithm.

SUMMARY OF THE INVENTION

The present invention provides a computer-implemented method for encoding a digital n-bit gray scale image data stream (where $9 \leq n \leq 24$) into an RGB encoded 8-bit image data stream, comprising the steps of: accessing each gray scale image data pixel of said n-bit data stream sequentially, applying 3 mathematical transformations to each of n-bit luminance values retrieved from said gray scale image data pixels, storing the results of said mathematical transformations into three 8-bit sub-pixel memory locations as an 8-bit RGB encoded image data pixel, outputting said 8-bit RGB encoded image data pixels sequentially as an 8-bit RGB encoded image data stream, characterized in that, said 3 mathematical transformations applied to each n-bit pixel data value are defined as:

$$R = \sqrt[3]{v} * s$$

$$G = \sqrt{\frac{v * s}{R}} * s$$

$$B = \frac{v * s^3}{R * G},$$

wherein v is the n-bit luminance value (9-24-bit) stored in a data pixel of the original digital high quality gray scale image, s is a scaling factor depending on the bit range of the gray value, and R, G and B are respectively the 8-bit values of the three 8-bit pixel channels in an RGB-encoded image. The present invention provides a computer-implemented method for decoding a digital n-bit gray scale image data stream (where $9 \leq n \leq 24$) from an RGB encoded 8-bit image data stream, comprising the steps of: accessing the three sub-pixel values stored in each RGB 8-bit image data pixel of said RGB encoded 8-bit image data stream sequentially, applying a mathematical transformation to said three sub-pixel values, storing the result of said mathematical transformation in a single channel n-bit gray scale image data pixel, outputting said n-bit image pixels sequentially as a high quality gray scale image data stream, characterized in that, said mathematical transformation applied to said three sub-pixel values is defined as:

$$v_L = \frac{R * G * B}{s^3},$$

wherein $v_L$ is the calculated n-bit luminance value, s is a scaling factor depending on the bit range of the gray value, and R, G and B are respectively the 8-bit values of the three 8-bit pixel channels in an RGB-encoded image.

A straight-forward attempt to reduce file size by applying lossy JPEG compression results in inacceptable damage to the data, as the compression algorithm to process the image makes the wrong assumption that it deals with a normal RGB-image.

Therefore, as disclosed by this invention, an encoding and decoding algorithm is used to convert the gray scale image temporarily into an RGB color formatted image file, on which the lossy JPEG compression can be applied without causing harm to the diagnostic image content. The defining step taken in this conversion from grayscale (single channel) image data to RGB (triple channel) color data is the application of specifically designed mathematical transformations which allow the gray scale luminance data to "survive" the subsequent steps performed during color JPEG compression:

- a color space transformation into $Y'C_BC_R$,
- a reduction of the spatial resolution of the $C_B$ and $C_R$ components (chroma subsampling),
- block splitting (each channel is split into 8×8 pixel blocks)
- dicrete cosine transformation,
- quantization,
- and, entropy encoding.

To this effect, only very specific mathematical functions as disclosed here can be applied, which intrinsically safeguard the stored 3-channel data from affecting the quality of the final decoded high quality gray scale image. In order to achieve the best compression ratios, it has been found that the mathematical transformations which map the n-bit value into 3 8-bit values, so that the there is little color variance in the resulting color pixel give the best results in terms of file size compression. In other words, the mathematical transformations which transform the n-bit pixel value into an 8-bit RGB pixel which is as close as possible to a gray color value, will give the best compression results.

This invention is advantageous in that it allows high quality gray scale image data to be compressed (and thus dramatically reduced in size) by the very efficient standard compression algorithms such as JPEG lossy compression without dramatically compromising the image quality. At the same time, the invention allows the original image (n-bit) to become available to client application software after decoding the image into its full bit depth. This means that the full dynamic range image is available for the client software on which for instance window-level operations can be performed in real time.

In the context of the present invention, digital n-bit gray scale image data has to be understood as digital data which is structured as such that it can hold or contain the pixel data of a digital image and where each pixel is represented by an n-bit memory position, holding an n-bit value representing the luminance value for the pixel. An n-bit value can represent $2^n$ different shades of gray. For example, a 10-bit pixel can represent a luminance value between 0 and 1023. The digital data may be presented as a continuous stream of pixels representing a single image or a series of multiple images (an image data stream), or a delimited data file which represents one single image (an image data file).

In the context of this invention, an image data pixel has to be understood as a the smallest discrete memory location in a digital image data stream representing the luminance value of 1 pixel element of a digital image.

An 8-bit encoded RGB image, is a digital image stored using the additive RGB color model. In the RGB color model, three color channels are used to store red, green, and blue values in varying amounts to represent each available color that can be reproduced. Adjusting the relative balance of values in these color channels adjusts the color being represented. When all three values are equal, the result is a neutral tone, from black through gray to white. An 8-bit encoded RGB pixel consists of three 8-bit subpixels or memory locations representing one of the three (R, G or B) color channel values as an 8-bit value.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to here as computer systems) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

The present invention can be implemented as a computer program product adapted to carry out the steps set out in the description. The computer executable program code adapted to carry out the steps set out in the description can be stored on a computer readable medium.

Specific examples and preferred embodiments are set out in the dependent claims.

Further advantages and embodiments of the present invention will become apparent from the following description and drawings.

BRIEF DESCRIPTION OF THE DRAWINGS

FIG. 1 shows a flowchart illustrating the encoding [1002] and compression [1004] steps used in a medical application. In the embodiment shown, the encoding and compression takes place at the server side [1000] of the application, and the standard decompression [2001] and decoding [2003] takes place in the browser application [2000]. This flowchart thus illustrates an embodiment of the described encoding scheme disclosed in this application, allowing that a digital medical image can be encoded and compressed on the server side for optimal network transfer [1005] of the image data to a web browser client software, which can decompress and decode the encoded image for further use or processing [2005] by the browser.

DETAILED DESCRIPTION OF THE PREFERRED EMBODIMENTS

In the following detailed description, reference is made in sufficient detail to the above referenced drawings, allowing those skilled in the art to practice the embodiments explained below.

Embodiments of the present invention provide a method for encoding a digital n-bit gray scale image data stream (where $9 \leq n \leq 24$) into an RGB encoded 8-bit image data stream. The image processing apparatus is typically implemented on a computer system comprising a means for inputting data (such as a keyboard, a touch screen, a computer mouse, a bar code scanner or other means), a means for storing the medical data (such as a computer memory), a processor for applying calculations, rules and comparisons on the data, and a means of displaying or storing the results such as a computer monitor, a printer, and/or an external computer memory.

Figure 1:
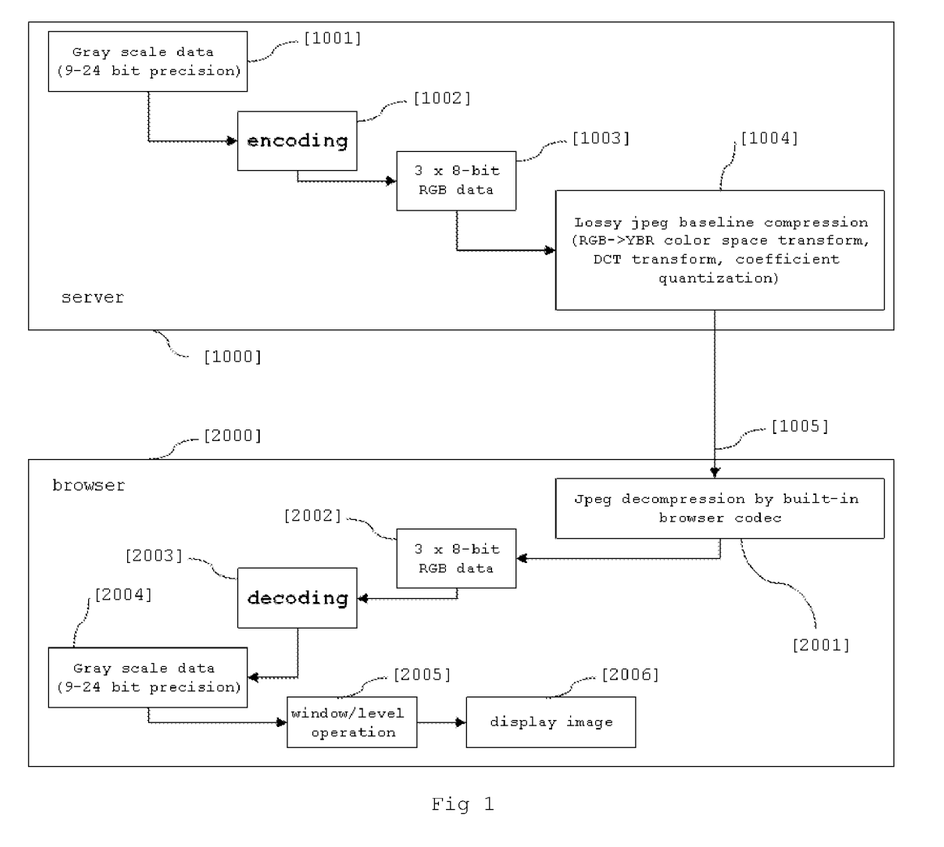

FIG. 1 shows in great detail the different steps which an original digital medical high resolution gray scale image undergoes when being encoded by the method as disclosed by this invention. The original n-bit gray scale image is presented to for encoding [1002] as gray scale image data [1001] with a bit depth between 9 and 24 bits). Images with lower bit depths then 9 can be stored in 1 byte and therefore do not require conversion or compression since each pixel already can fit within the minimal word length of a single byte. The encoding step is performed by the image processing means [20] of FIGS. 4 and 5, and will be discussed in greater detail below.

The result of the encoding step [1002] is an encoded 3×8-bit RGB data stream [1003] which is provided as an intermediary image format, but which is not directly useable in any image processing application. The intermediary image data stream or file cannot be discriminated from a standard 8-bit RGB color image, which is the reason why it can be processed by standard color image compression algorithms, such as a lossy jpeg baseline compression. And this is indeed the purpose of the conversion provided by the encoding [1002]; the intermediary image format formatted as an 8-bit RGB image can be compressed using the standard compression methods [1004] used in standard webserver and browser software.

The compressed intermediary image data stream can then be transferred more efficiently over a computer network [1005], after which the compressed intermediary image data [2002] are obtained after decompression performed by the standard jpeg decompression codec of the browser [2001]. The intermediary image data [2002] can then be decoded [2003] in order to obtain the original n-bit gray scale data [2004] which is used for further image processing steps [2005] and display [2006].

Figure 2:
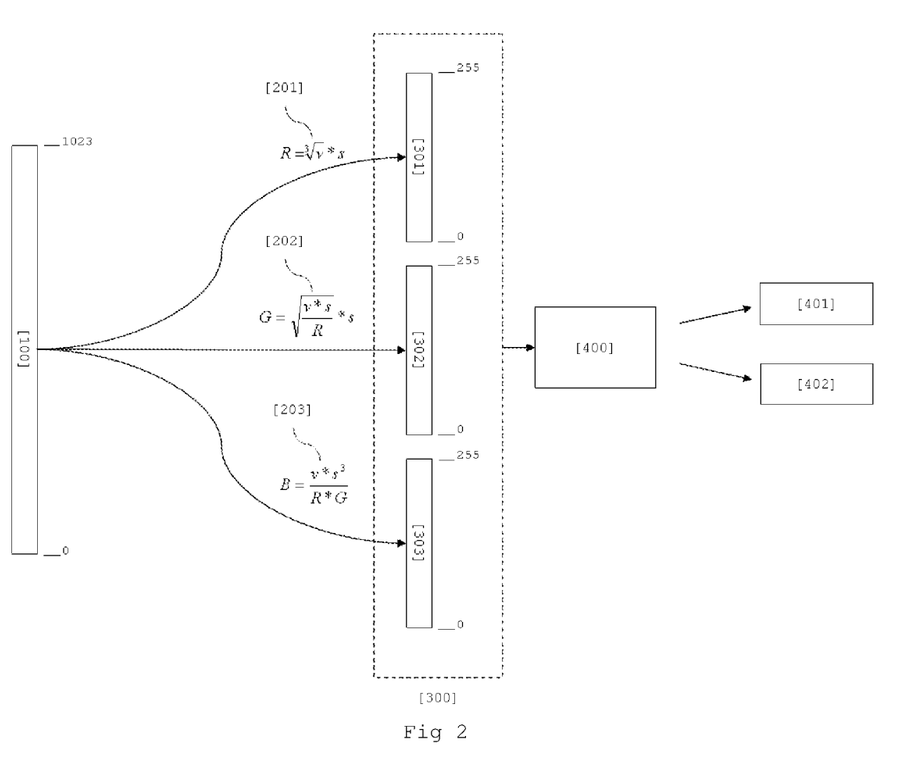
FIG. 2 shows a flowchart of an embodiment of this invention, where the encoding step is performed on one 10-bit gray scale image pixel as disclosed in claim 1 of this application. A 10-bit gray scale pixel value [100] is transformed into an RGB encoded 8-bit image pixel [300] consisting of 3 sub-pixel values [301], [302] and [303]. Subsequent image compression [400] can be applied after allowing more efficient image data storage [401] or image data network transfer [402].

FIG. 2 discloses the details of an embodiment of the encoding step of the original 10-bit gray scale image. In the diagram a 10-bit pixel value [100] is shown, which can be assigned a value between 0 and 1023. The n-bit pixel value is transformed into three 8-bit values by applying the three shown mathematical transformations [201], [202] and [203] to the original gray 10-bit value "v". Said three mathematical transformations are designed as such that their results fit the foreseen 8-bit values (between 0 and 255) of the three 8-bit subpixels [301], [302] and [303] of the RGB formatted intermediary data file [300]. It is therefore that a carefully chosen scaling factor "s" is introduced into the mathematical transformation functions. In the case that the bit range is for example 10, the multiplier "s" will ensure that the results of the mathematical transformations will never exceed the 8-bit range values between 0 and 255. It is obvious that a different scaling factor will need to be used in case of different bit ranges. The assumption is that the 8-bit bit range for the color channels are optimally used to store as much image information as possible.

Another very important aspect of the particular mathematical transformations is that the subsequently applied jpeg compression step [400] does not have an important impact on the image quality after decompression [500] and decoding [700] of the transferred [401] or stored [402] image data. The way that the transformations are shaped will determine the impact on the final image quality after a encoding-compression-decompression-decoding cycle. It is therefore that explicit reference is made to the formulas disclosed in FIG. 2 and FIG. 3 of this application, which do fulfill said requirements.

Figure 3:
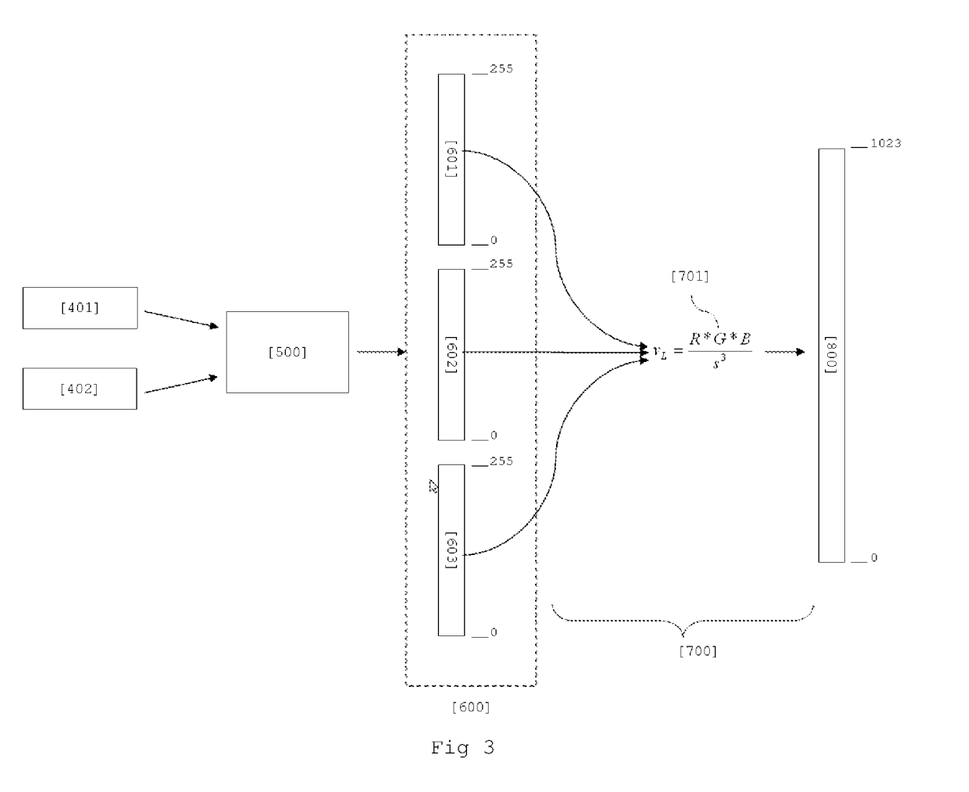
FIG. 3 shows a flowchart of an embodiment of this invention, where the decoding step is performed after the decompression step [500] of an RGB encoded 8-bit image pixel [600]. The RGB encoded 8-bit image is transformed into a 10-bit gray scale image pixel [800] by applying the transformation [701] on the three sub pixel values [601], [602] and [603] of the RGB encoded 8-bit image pixel [600] in a decoding step [700].

Another embodiment of the same invention may apply different mathematical transformation functions then the ones shown in FIG. 2 and FIG. 3, but having similar characteristics as mentioned above. These transformation functions for encoding may be formulated in a generic way as follows:

$$R=fn(v,s)$$

$$G=fn'(v,s,R)$$

$$B=fn''(v,s,R,G),$$

and wherein said mathematical transformation fn, fn' and fn" are defined as such that when $$(R,G,B)=(x+dr,x+dg,x+db),$$

the values of dr, dg, db are preferably as close to 0 as possible.

The decoding transformation function could then be formulated as:

$$v_L=fn_r(R,G,B,s)$$

FIG. 3 discloses the details of an embodiment of the decoding step of the 8-bit RGB encoded image. In the diagram the compressed RGB data are received and decompressed [500] after transfer [401] or storage [402] of the compressed RGB data. The decompressed 8-bit RGB data [600] are decoded [700] into a 10-bit pixel value [800], by applying mathematical transformation [701] to the 8-bit sub pixel data [601], [602] and [603].

Figure 4:
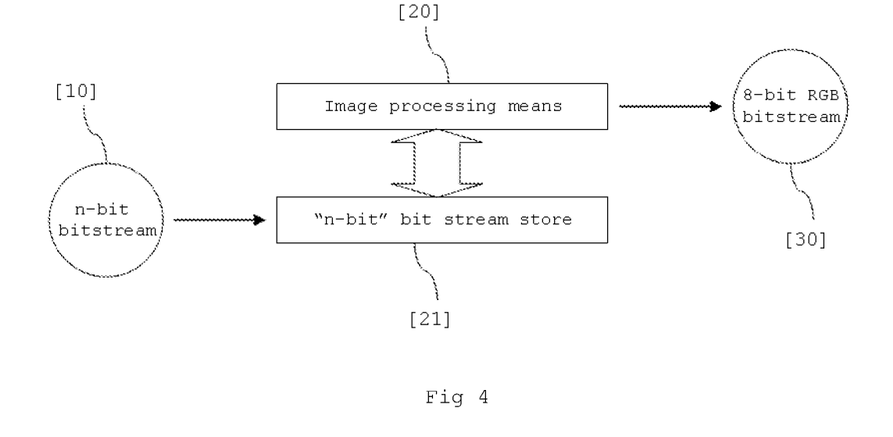
FIG. 4 illustrates schematically an embodiment of the invention which comprises an "n-bit" bit stream store [21] which reads in the n-bit bitstream [10] representing the original n-bit image data. An image processing means or processor [20] has access to the bit stream store [21] and is configured to perform mathematical transformations on the content of the bit stream store. The image processing means converts the original n-bit image data into the 8-bit RGB bitstream.
Figure 5:
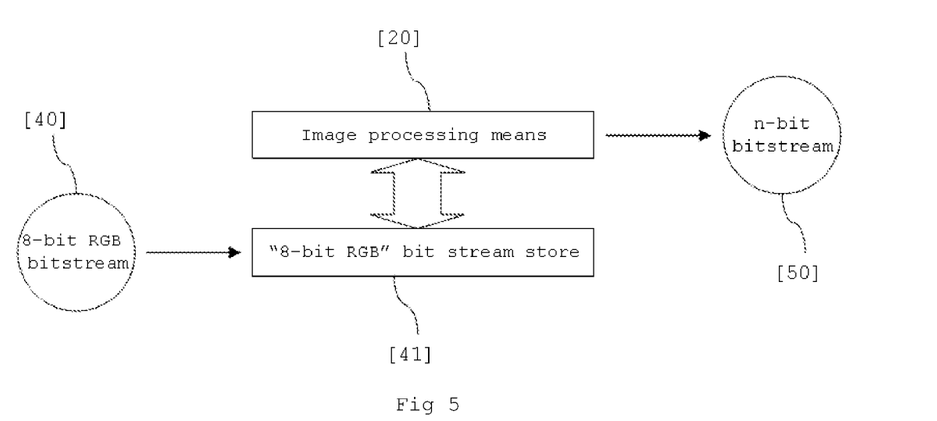
FIG. 5 illustrates schematically an embodiment of the invention which comprises an 8-bit RGB bit stream store [41] which reads in the 8-bit RGB bitstream [40] representing a (previously decompressed) 8-bit RGB image. An image processing means or processor [20] has access to the bit stream store [41] and is configured to perform mathematical transformations on the content of the bit stream store. The image processing means converts the 8-bit RGB image data into the original n-bit bit stream [50].

FIGS. 4 and 5 illustrate an embodiment of the invention comprising at least an image processing means (or processor) [20] and a bit stream store [21] and [41] which are configured to perform respectively the encoding and decoding operations as described before. The bit stream store is connected to the image processing means which is configured to retrieve the image data bit stream for encoding, and respectively, decoding. The bit stream store allows the image data bit stream to be read out by the image processing means [20] sequentially, i.e. byte-per-byte, so it can perform the mathematical transformations on each byte of image information as explained above. The resulting output from the encoding process performed by the image processing mean [20] is the 8-bit RGB bit stream [30], whereas from the decoding process, the resulting output is the n-bit bit stream [50].

In order to illustrate the performance of the described invention, measurements have been performed on a set of reference grayscale medical images for which the compression (image) quality and size have been compared to known compression techniques. The reference images themselves were 12-bit grayscale images.

Figure 6:
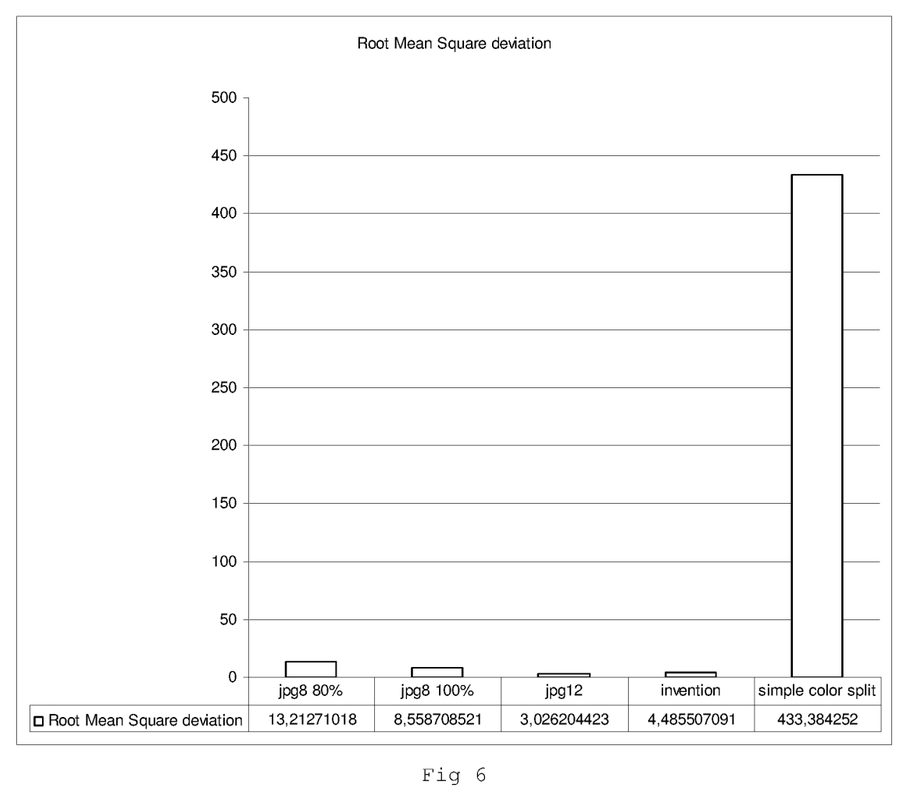
FIG. 6 shows the compression result (expressed in RMS) achieved by the different tested algorithms against the new algorithm (indicated as "invention").

FIG. 6 shows the compression result (expressed in RMS) achieved by the different tested algorithms against the new algorithm (indicated as "invention"). The compression performance is measured as the resulting file size (which should be as small as possible) after compression of a selected reference image The different tested algorithms are the following:

jpg8 80%: baseline jpg compression on the 8 most significant bits of the image where compression quality setting is 80% (lossy)

jpg8 100%: baseline jpg compression on the 8 most significant bits of the image where compression quality setting is 100% (lossless)

jpg12: 12-bit gray scale jpg-encoding scheme (supported by the jpg-standard, but not implemented in standard internet browsers)

invention: cubic root encoding of the 12-bit grayscale into 8-bit RGB encoded image, followed by regular jpg-RGB compression scheme.

simple color split: separation of lower 8 bits in one color channel, and highest 4 bit in another color channel, followed by regular color baseline jpg compression scheme. This method is illustrates the scenario where no encoding (or at least no suitable encoding) takes place before the jpg-RGB compression.

The compression quality results achieved by the "simple color split" method clearly show that arbitrarily chosen conversion into an RGB-formatted pixel stream does not achieve usable results. This is a clear indication that the data values are severely distorted in the case that no appropriate transformation is chosen before the standard baseline jpg-compression is applied.

The "jpg12" compression technique is clearly the reference technique to compare our invention against as this method compresses the full color range of 12-bits. This algorithm is however not a standard supported method supported by standard web browsers.

The compression quality of our invention still clearly exceeds the qualities achieved by applying the so-called 8-bit compression methods tested. 8-bit compression methods only perform their compression through the compression of only the most significant 8 bits, which proves that our method is clearly superior to these standard approaches.

Figure 7:
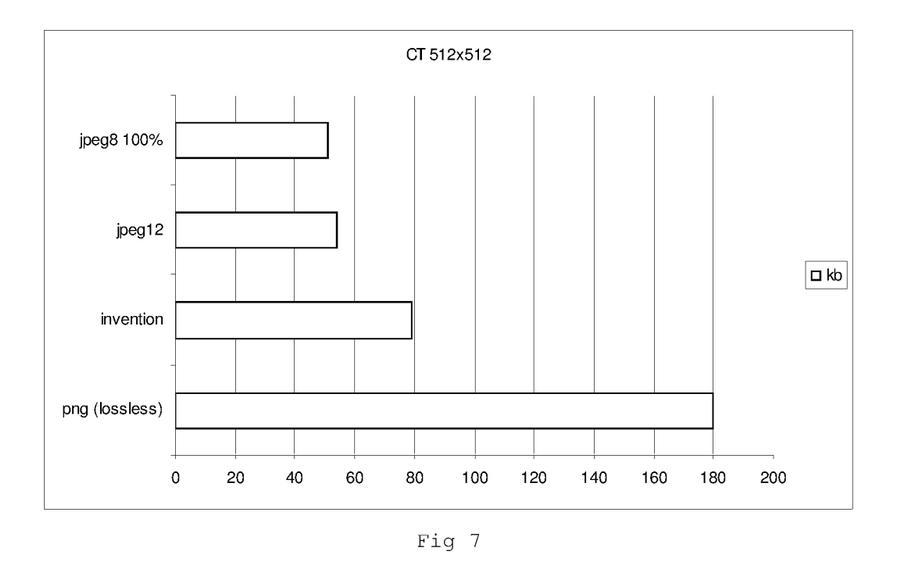
FIGS. 7 and 8 show the resulting size of the compressed 2 reference medical images as achieved by the encoding transformations followed by an RGB-jpg compression as measured in comparison with other standard compression algorithms.
Figure 8:
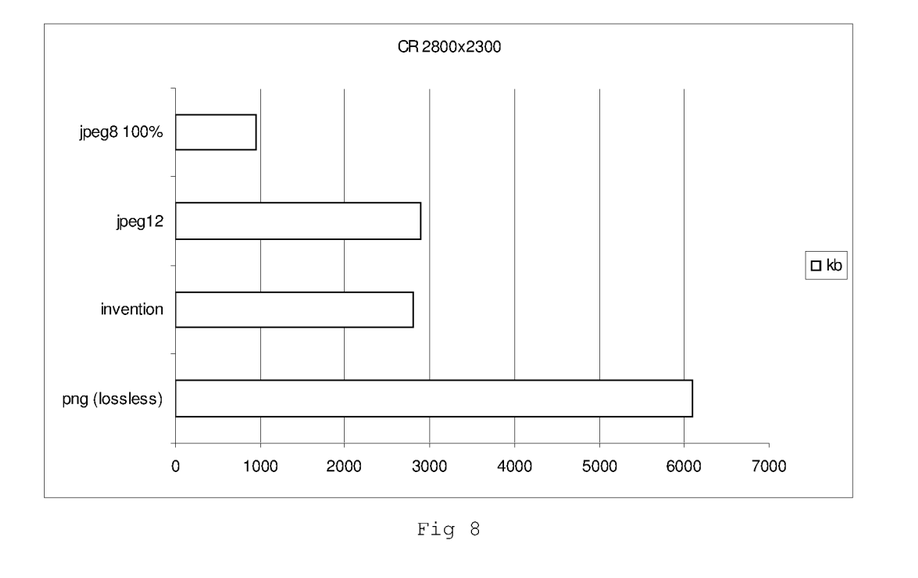

FIGS. 7 and 8 show the resulting size of the compressed 2 reference medical images as achieved by the encoding transformations followed by an RGB-jpg compression as measured in comparison with other standard compression algorithms. The first graph shows the compression result of a 12-bit gray scale 512×512 CT image, whereas the second graph concerns a 12-bit gray scale 2800×2300 CR image.

The results indicate that the 8-bit jpg compression methods appear to be obviously the most performing one, but they achieve this high compression rate thanks to the fact that they discard ⅓ of the image information a priori, which is unacceptable for compression methods used in a diagnostic context. The compression achieved by the new algorithm is comparable to what can be achieved through 12-bit jpg compression.

The invention claimed is:

1. A method for encoding and compressing a single channel digital n-bit gray scale image data stream, in which 9≤n≤24, into an 8-bit RGB encoded image data stream, the method comprising the steps of:
sequentially accessing each of a plurality of gray scale image data pixels of the digital n-bit gray scale image data stream;
applying three mathematical transformations to each of a plurality of n-bit luminance values retrieved from the plurality of gray scale image data pixels;
storing results of the three mathematical transformations into three 8-bit sub-pixel memory locations as 8-bit RGB encoded image data pixels;

sequentially outputting the 8-bit RGB encoded image data pixels as the 8-bit RGB encoded image data stream; and compressing the 8-bit RGB encoded image data stream using a JPEG standard;

wherein the three mathematical transformations are defined as:

$$R = \sqrt[3]{v} * s$$

$$G = \sqrt{\frac{v*s}{R}} * s$$

$$B = \frac{v*s^3}{R*G}$$

v is the n-bit luminance value (9-24-bit) stored in a data pixel of an original digital high quality gray scale image;

s is a scaling factor depending on a bit range of the gray value; and

R, G, and B are respectively 8-bit values of three 8-bit pixel channels in the 8-bit RGB encoded image data stream.

2. An image processing apparatus comprising:

a bit-stream storage that stores an n-bit image data stream; and an image processor that communicates with the bit-stream storage; wherein the image processor is configured or programmed to perform the steps of the method according to claim 1.

3. A non-transitory computer readable medium comprising data stored on the non-transitory computer readable medium that, when interpreted and executed by a computer, includes a bit-stream storage that stores an n-bit image data stream and an image processor that communicates with the bit-stream store and performs the steps of the method according to claim 1.

4. A method for uncompressing and decoding a single channel digital n-bit gray scale image data stream, in which $9 \leq n \leq 24$, from an 8-bit RGB encoded image data stream, the method comprising the steps of:

sequentially accessing three sub-pixel values stored in each of a plurality of 8-bit RGB image data pixels of the 8-bit RGB encoded image data stream;

uncompressing the 8-bit RGB encoded image data stream using a JPEG standard;

applying a mathematical transformation to the three sub-pixel values;

storing a result of the mathematical transformation in a single channel n-bit gray scale image data pixel; and sequentially outputting n-bit image pixels as a high quality gray scale image data stream; wherein the mathematical transformation applied to the three sub-pixel values is defined as:

$$v_L = \frac{R*G*B}{s^3}$$

$v_L$ is a calculated n-bit luminance value;

s is a scaling factor depending on a bit range of the gray value; and

R, G, and B are respectively 8-bit values of three 8-bit pixel channels in the 8-bit RGB encoded image data stream.

5. An image processing apparatus comprising:

a bit-stream storage that stores an 8-bit RGB encoded image data stream; and an image processor that communicates with the bit-stream storage; wherein the image processor is configured or programmed to perform the steps of the method according to claim 4.

6. A non-transitory computer readable medium comprising data stored on the non-transitory computer readable medium that, when interpreted and executed by a computer, includes a bit-stream storage that stores an 8-bit RGB encoded image data stream and an image processor that communicates with the bit-stream storage and performs the steps of the method according to claim 4.

* * * * *